United States Patent [19]
Tomisaki et al.

[11] Patent Number: 6,152,598
[45] Date of Patent: Nov. 28, 2000

[54] R/F AND CHEST RADIOGRAPHY COMPATIBLE X-RAY IMAGING TABLE

[75] Inventors: Takayuki Tomisaki; Shinichi Yamada, both of Tochigi, Japan

[73] Assignee: Kabushiki Kaisha Toshiba, Kawasaki, Japan

[21] Appl. No.: 09/145,219

[22] Filed: Sep. 1, 1998

[30] Foreign Application Priority Data

Sep. 2, 1997 [JP] Japan ................................. 9-237155

[51] Int. Cl.$^7$ ....................................................... A61B 6/04
[52] U.S. Cl. ........................ 378/209; 378/188; 378/189; 5/601
[58] Field of Search .................... 378/209, 188, 378/189; 5/601

[56] References Cited

U.S. PATENT DOCUMENTS

| | | |
|---|---|---|
| 2,707,662 | 5/1955 | Goldfield et al. . |
| 4,689,487 | 8/1987 | Nishiki et al. . |
| 5,014,292 | 5/1991 | Siczek et al. . |
| 5,877,501 | 3/1999 | Ivan et al. . |
| 5,883,937 | 3/1999 | Schmitt .................................. 378/98.8 |

*Primary Examiner*—David P. Porta
*Assistant Examiner*—Paul R. Hobden
*Attorney, Agent, or Firm*—Oblon, Spivak, McClelland, Maier & Neustadt, P.C.

[57] ABSTRACT

A main body of a diagnostic table apparatus holds a supporting body slidably. The supporting body holds an X-ray tube and an X-ray flat panel detector so as to face each other. A tabletop of the diagnostic table is fitted rotatably to the main body of the diagnostic table apparatus via a hinge as a diagnostic table withdrawing mechanism. In case a chest radiography is to be taken in a standing position, the tabletop of the diagnostic table is withdrawn, an X-ray is irradiated from the back of the subject who faces an X-ray flat panel detector and puts his or her chin on a chin holder.

8 Claims, 10 Drawing Sheets

R/F AND CHEST RADIOGRAPHY COMPATIBLE X-RAY IMAGING TABLE

BACKGROUND OF THE INVENTION

1. Field of the Invention

The present invention relates to an X-ray imaging equipment for picking up two dimensional images based on a spatial distribution of X-rays transmitted through a subject and, more particularly, an X-ray imaging equipment having an X-ray flat panel detector.

2. Description of the Prior Art

In the prior art, there has been employed a general-purpose X-ray imaging equipment which comprises an I.I.-TV system having an image intensifier (abbreviated as "I.I." hereinafter) and a TV camera, and a film changer. Such X-ray imaging equipment is available in both an X-ray fluoroscopy and an X-ray radiography.

The X-ray imaging equipment is equipped with a diagnostic table on which a subject is put and which can move to stand and lay down. In a diagnosis of the digestive system, a contrast medium such as barium which is taken by the subject can be projected from various angles.

Normally such X-ray imaging equipments are classified into an over-table tube type X-ray imaging equipment (see FIG. 1) wherein an X-ray tube is positioned over a tabletop of a diagnostic table and a detector is positioned below the tabletop when the tabletop is positioned horizontally, and an under-table tube type X-ray imaging equipment (see FIG. 2) wherein the X-ray tube is positioned below the tabletop and the detector is positioned over the tabletop when the tabletop of the diagnostic table is positioned horizontally.

Figure 1:
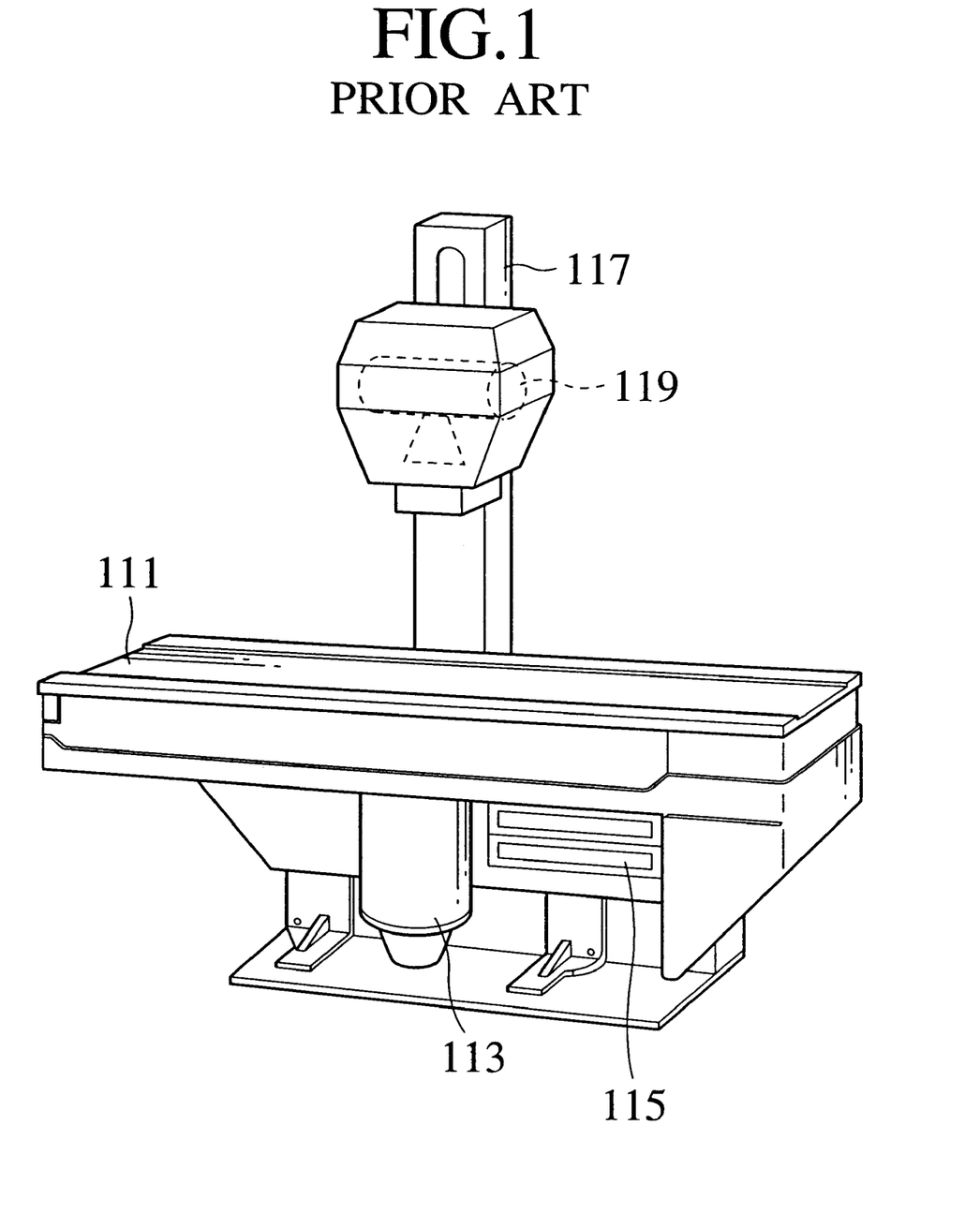
FIG. 1 is a perspective view showing an over-table tube type X-ray imaging equipment in the prior art.
Figure 2:
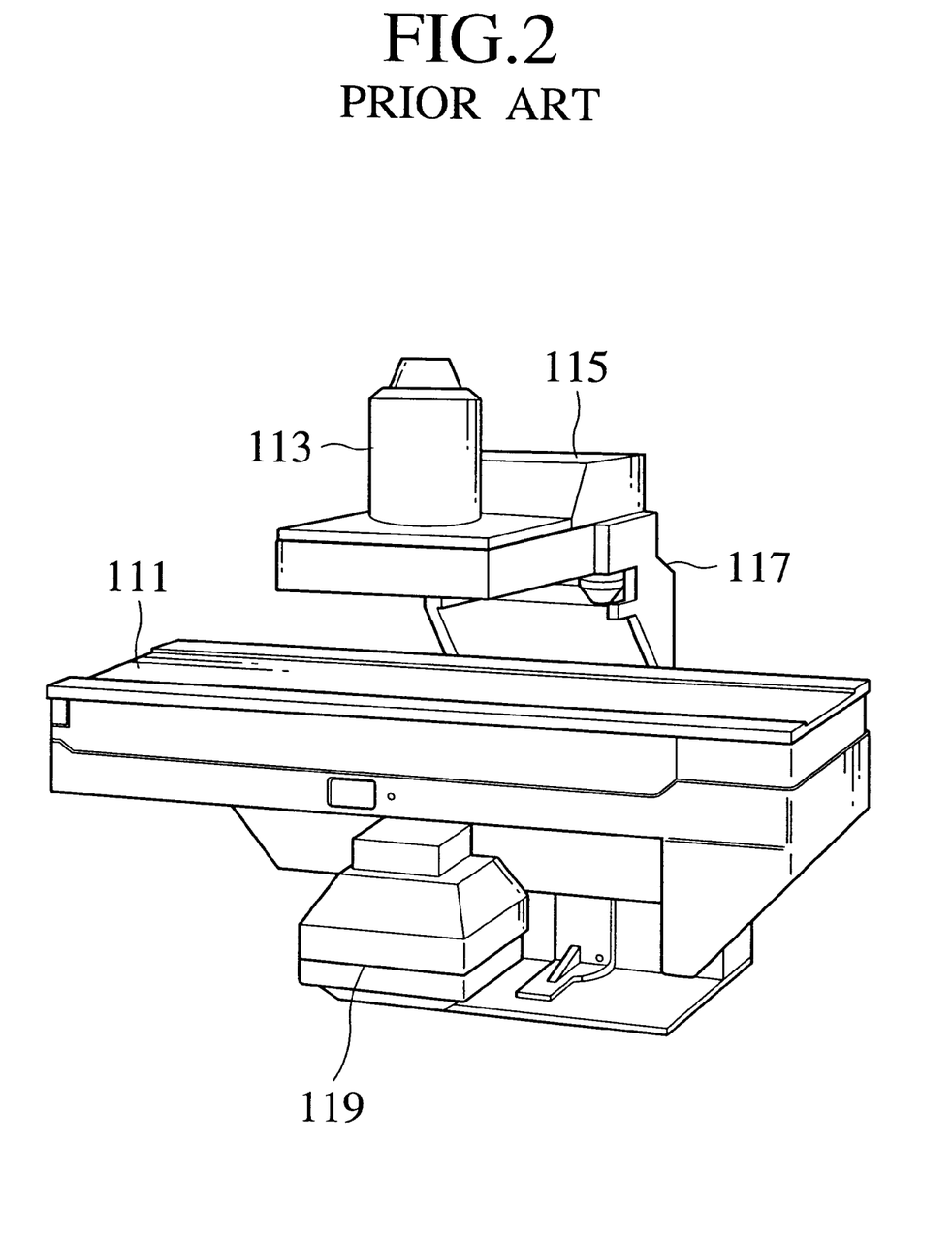
FIG. 2 is a perspective view showing an under-table tube type X-ray imaging equipment in the prior art.

The over-table tube type and under-table X-ray imagine equipment includes a diagnostic table 111, an I.I.-TV system 113, a film changer 115, a supporting body 117 and an X-ray tube 119.

In the over-table tube type X-ray imaging equipment employing the I.I.-TV system in the prior art, in the case that a chest radiography of the subject in an upright position of the diagnostic table is to be taken, a distance between the subject and an X-ray tube 119 can not sufficiently be kept because an I.I.-TV system 113 interferes with an inner wall of the building because of its size especially its depth.

Meanwhile, according to the normal imaging method in the chest radiography, an X-ray film or an X-ray detector is displaced in front of the subject in a standing position, and then an X-ray is irradiated to the subject from the back of the subject at a certain distance. However, in the case that the chest radiography is taken by the above over-table tube type X-ray imaging equipment, face or other portions of the subject interfere with a diagnostic table 111 when the subject tries to turn his or her back on the X-ray tube 119. Therefore, the chest radiography must be taken while turning the face of the subject laterally, which results in different postures of the neck and the chest of the subject from those in the normal radiography. In other words, it has been unreasonable to employ the above over-table tube type X-ray imaging equipment as the chest radiographic equipment.

In addition, in the X-ray imaging equipment in the prior art, the diagnostic table has not been able to be easily exchanged.

In the meanwhile, in the under-table tube type X-ray imaging equipment, an imaging device equipped with the I.I.-TV system 113 and the film changer 115 is provided over the diagnostic table 111, and the space between the imaging surface of the imaging device and the diagnostic table 111 is narrow in order to make the imaging surface close to the subject. Therefore, it is difficult for the subject whose physical strength is declined and the handicapped subject to get on or down from the diagnostic table 111 and further it is difficult for a doctor or a technical expert to get access to the subject.

Recently a technology of a thin and lightweight X-ray flat panel detector using a semiconductor technology has been disclosed (see U.S. Pat. No. 4,689,487).

This X-ray flat panel detector comprises semiconductor detector elements which are arranged to correspond to pixels aligned in a matrix fashion. The semiconductor detector elements detect X-ray directly, or indirectly in the form of visual light by means of fluorescent material, and then the detected X-ray is read as image signals via switching gates such as thin film transistors (TFTs), or the like.

The X-ray flat panel detector in which the X-ray is directly converted into a charge per pixel and then read out is called a direct conversion type X-ray flat panel detector. In contrast, the X-ray flat panel detector in which the X-ray is converted into visual light by the fluorescent material, etc., then the visual light is converted into the charge per pixel, and then read out is called an indirect conversion type X-ray flat panel detector.

Figure 3:
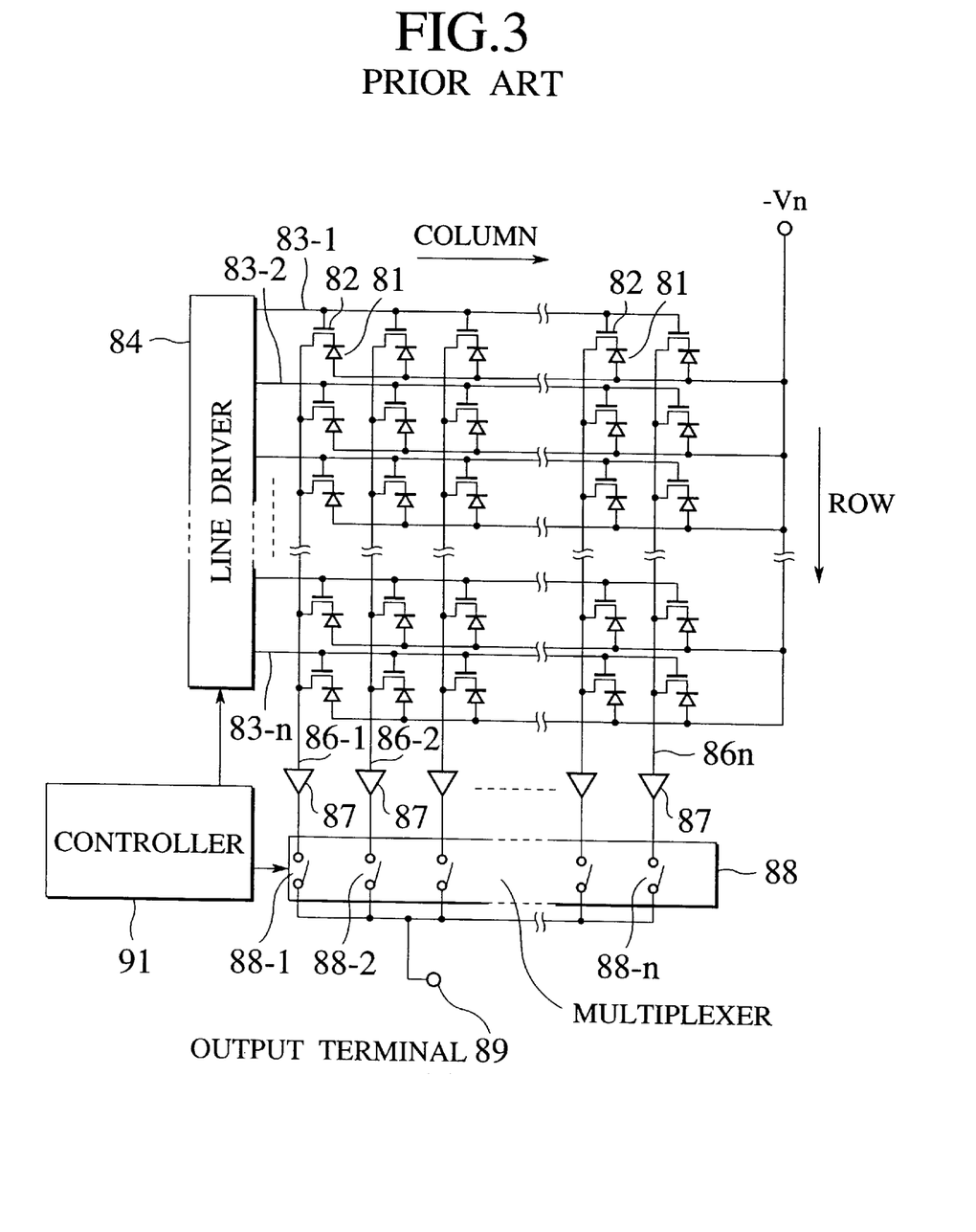
FIG. 3 is a block circuit diagram showing a configuration of an X-ray flat panel detector.

FIG. 3 is a block circuit diagram showing a representative configuration of the indirect conversion type X-ray flat panel detector. Such X-ray flat panel detector detects two dimensional distribution of the light which has been converted from the X-ray to a visible light by the fluorescent material (not shown).

As shown in FIG. 3, each of the pixels which are arranged in a two-dimensional matrix fashion comprises a PIN photo diode (abbreviated as "PD" hereinafter) 81 for converting the intensity of the light into the charges and accumulating them, and a thin film transistor (abbreviated as "TFT" hereinafter) 82 as a switching device for reading the accumulated charges from the PD 81 as the image signal.

An anode of the PD 81 is connected to a common bias voltage (−Vn). A cathode of the PD 81 is connected to a source of the corresponding TFT 82. Respective gates of the TFTs 82 aligned on the same row are connected commonly to one of line driver signal lines 83 (83-1, 83-2, . . . , 83-n), and the TFTs 82 are driven sequentially into their reading state by a line driver 84. Respective drains of the TFTs 82 aligned on the same column are connected commonly to one of read signal lines 86 (86-1, 86-2, . . . , 86-n). The read signal lines 86-1, 86-2, . . . , 86-n are connected to a multiplexer 88 via charge amplifiers 87 respectively. The multiplexer 88 multiplexes signals output from the read signal lines 86-1, 86-2, . . . , 86-n and then outputs them as an imaging signal output 89.

When the TFTs 82 are set into their reading state by driving sequentially the line driver signal lines 83-1, 83-2, . . . , 83-n by the line driver 84 and supplying the voltage to the gates of the TFTs 82 on respective rows, the charges read out pixel by pixel are amplified by the charge amplifiers 87, then multiplexed by the multiplexer 88, and then output as X-ray image signals. The line driver 84 and the multiplexer 88 are controlled by a controller 91.

As described above, according to the over-table tube type X-ray imaging equipment employing the I.I.-TV system in the prior art, there has been such a problem that, if the chest radiography of the subject is to be taken in an upright position of the diagnostic table, a sufficient distance between the subject and the X-ray tube can not kept because the I.I.-TV system interferes with an inner wall of the building because of its size, especially its depth.

Further, if the chest radiography is to be taken by the above over-table tube type X-ray imaging equipment, the face, etc. of the subject interfere with the diagnostic table when the subject tries to turn his or her back on the X-ray tube. Therefore, there has been another problem that the subject cannot assume the normal posture for the chest radiography.

Furthermore, in the X-ray imaging equipment in the prior art, there has been still another problem that exchange of the diagnostic table is not ready.

Moreover, in the under-table tube type X-ray imaging equipment employing the I.I.-TV system in the prior art, the space is narrow between the diagnostic table and the imaging surface of the I.I.-TV system and the film changer. Therefore, there has been yet still another problems that it is difficult for the subject whose physical strength is declined and the handicapped subject to get on or down from the diagnostic table and it is difficult for a doctor or a technical expert to get access to the subject.

SUMMARY OF THE INVENTION

In view of the above problems, it is an object of the present invention to provide an X-ray imaging equipment which is able to make a chest radiography of a subject in a relaxed posture in an over-table tube type X-ray imaging equipment.

It is another object of the present invention to provide an X-ray imaging equipment which is able to keep a distance between the subject and an X-ray tube sufficiently.

It is still another object of the present invention to provide an X-ray imaging equipment in which an exchange of a diagnostic table can be performed easily.

In order to achieve the above objects, there is provided an X-ray imaging equipment comprising: a tabletop of a diagnostic table on which a subject is loaded; an X-ray generating means provided on a front surface side of the tabletop of the diagnostic table; an X-ray flat panel detector provided on a back surface side of the tabletop of the diagnostic table; a supporting body for holding the X-ray generating means and the X-ray flat panel detector so as to face each other; and a tabletop supporting means for so supporting the tabletop of the diagnostic table as to be withdrawn from an X-ray irradiating path from the X-ray generating means to the X-ray flat panel detector.

According to the above configuration, in the over-table tube type X-ray imaging equipment according to the present invention, because the thin X-ray flat panel detector is employed, the distance between the X-ray tube and the detector can be kept sufficiently in the chest radiography.

Also, in the over-table tube type X-ray imaging equipment according to the present invention, because the tabletop can be withdrawn, interference of the diagnostic table with the face of the subject can be eliminated at the time of the chest radiography, so that the radiography of the subject in his or her relaxed posture can be taken.

In the preferred embodiment of the present invention, the tabletop supporting means turns the tabletop of the diagnostic table around an axis which is parallel with a long side of the tabletop of the diagnostic table.

In the preferred embodiment of the present invention, the tabletop supporting means moves the tabletop of the diagnostic table in parallel with its tabletop surface.

In the preferred embodiment of the present invention, the supporting body holds the X-ray flat panel detector to move back and forth against the X-ray generating means.

In order to achieve the above objects, there is provided an X-ray imaging equipment comprising: a tabletop of a diagnostic table on which a subject is loaded and which can be split into at least two parts; an X-ray generating means provided on a front surface side of the tabletop of the diagnostic table; an X-ray flat panel detector provided on a back surface side of the tabletop of the diagnostic table; a supporting body for holding the X-ray generating means and the X-ray flat panel detector so as to face each other; and a tabletop supporting means for so supporting the tabletop of the diagnostic table as to be able to withdraw a portion of the tabletop of the diagnostic table which corresponds to a head of the subject.

In the preferred embodiment of the present invention, the tabletop supporting means turns the portion of the tabletop of the diagnostic table, which corresponds to the head of the subject, around an axis which is parallel with a long side of the tabletop of the diagnostic table.

In the preferred embodiment of the present invention, the diagnostic table withdrawing means moves the portion of the tabletop of the diagnostic table, which corresponds to the head of the subject, in parallel with its tabletop surface.

In order to achieve the above objects, there is provided an X-ray imaging equipment comprising: a tabletop of a diagnostic table on which a subject is loaded; an X-ray flat panel detector provided on a front surface side of the tabletop of the diagnostic table; an X-ray generating means provided on a back surface side of the tabletop of the diagnostic table; a supporting body for holding the X-ray generating means and the X-ray flat panel detector so as to face each other; and a detector supporting means for so supporting the X-ray flat panel detector as to be withdrawn from the front surface side of the tabletop of the diagnostic table.

In the under-table tube type X-ray imaging equipment according to the present invention, since the X-ray flat panel detector can be withdrawn from an area over the diagnostic table, it becomes easy for the subject whose physical strength is declined and the handicapped subject to board or get off the diagnostic table and it also becomes easy for a doctor or a technical expert to get access to the subject. In addition, in the radiography/fluoroscopy after the X-ray flat panel detector has been returned from its withdrawn state, since only the thin and lightweight X-ray flat panel detector must be positioned over the subject, a coercive impression against the subject can be eliminated and safety can be improved.

In the preferred embodiment of the present invention, the detector supporting means turns the X-ray flat panel detector around an axis which is parallel with a certain side of the X-ray flat panel detector.

In order to achieve the above objects, there is provided an X-ray imaging equipment comprising: an X-ray generating means; an X-ray flat panel detector; a supporting body for holding the X-ray generating means and the X-ray flat panel detector so as to face each other; a main body for holding the supporting body movably; and a diagnostic table detachably attached to the main body so as to be displaced between the X-ray generating means and the X-ray flat panel detector.

According to the present invention, since the diagnostic table can be separated, a space around the X-ray imaging equipment can be assured widely. Also, since the subject can be put on the diagnostic table or taken down from the diagnostic table at the position remote from the X-ray imaging equipment, the diagnostic table can be loaded onto the X-ray imaging equipment or unloaded from the X-ray imaging equipment in the situation that the subject is laid down on the diagnostic table. If a plurality of diagnostic tables are prepared, the subject can be exchanged smoothly.

In the preferred embodiment of the present invention, the main body has a diagnostic table holding arm to which the diagnostic table is fitted.

In the preferred embodiment of the present invention, the supporting body holds the X-ray flat panel detector to move back and forth against the X-ray generating means.

In the preferred embodiment of the present invention, the tabletop is a tabletop of a diagnostic table for carrying a subject thereon.

The nature, principle and utility of the invention will become more apparent from the following detailed description when read in conjunction with the accompanying drawings.

DESCRIPTION OF THE PREFERRED EMBODIMENTS

Embodiments of the present invention will be explained in detail with reference to the accompanying drawings hereinafter.

Figure 4:
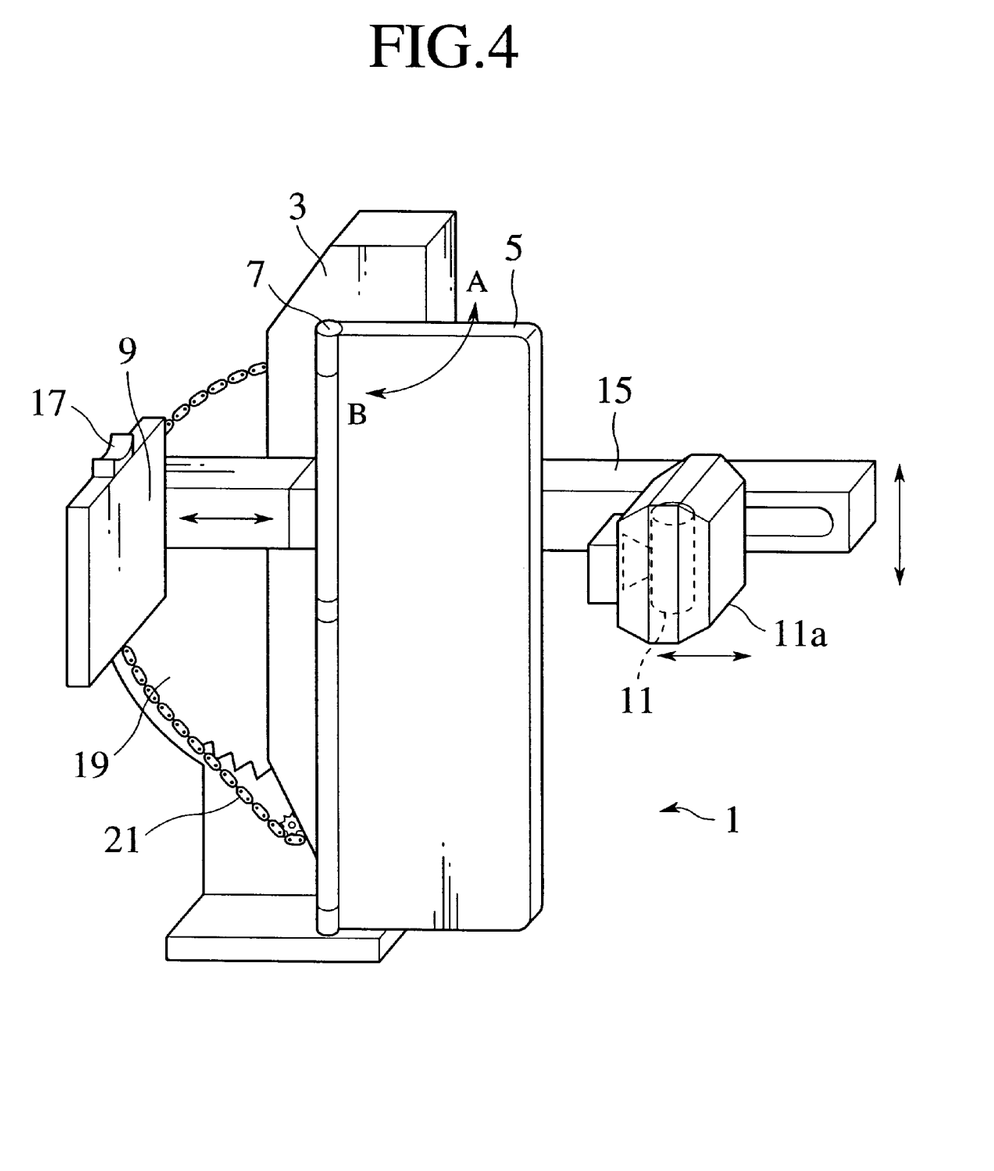
FIG. 4 is a perspective view showing an X-ray imaging equipment according to a first embodiment of the present invention.

FIG. 4 is a perspective view showing an X-ray imaging equipment according to a first embodiment of the present invention, wherein a diagnostic table is in a standing position and also a tabletop of a diagnostic table is withdrawn.

In FIG. 4, an X-ray imaging equipment 1 comprises a main body 3 of a diagnostic table apparatus having a diagnostic table tilting function, a tabletop 5 of a diagnostic table on which a subject is loaded, a hinge 7 as a diagnostic table withdrawing means for fitting the tabletop 5 of the diagnostic table rotatably to the main body 3 of the diagnostic table apparatus, an X-ray flat panel detector 9, an X-ray tube 11, and a supporting body 15 for connecting the X-ray flat panel detector 9 and the X-ray tube 11 to the main body 3 of the diagnostic table apparatus.

The X-ray imaging equipment 1 is a so-called over-table tube type X-ray imaging equipment wherein, when the tabletop 5 of the diagnostic table is positioned horizontally, the X-ray tube 11 is positioned on a front surface side (upper side) of the tabletop 5 of the diagnostic table. The X-ray tube 11 covered with a tube cover 11a is fitted to the main body 3 of the diagnostic table apparatus via the supporting body 15 such that it can be moved relative to the tabletop of the diagnostic table in the vertical and longitudinal directions respectively.

The X-ray flat panel detector 9 is formed by installing a detector as shown in FIG. 3, for example, into a box acting also as a shielding. The X-ray flat panel detector 9 is displaced to face the X-ray tube 11 via the tabletop 5 of the diagnostic table such that it can be moved together with a movement of the X-ray tube 11 along the longitudinal direction of the tabletop 5 of the diagnostic table.

A chin holder 17 which holds a chin of the subject thereon at the time of a chest radiography is provided on a top of the X-ray flat panel detector 9.

The tabletop 5 of the diagnostic table is fitted to the main body 3 of the diagnostic table apparatus rotatably by a hinge 7 provided along a long side of the tabletop 5 via the supporting body 15. Accordingly, if the tabletop 5 of the diagnostic table is rotated by about 90° around an axis of rotation of the hinge 7 as represented by the bi-directed line A-B in FIG. 4, it can be moved out of an irradiation path from the X-ray tube 11 to the X-ray flat panel detector 9.

In FIG. 4, a reference 19 denotes a sector gear which is a part of a diagnostic table tilting mechanism and a reference 21 denotes a chain for driving the sector gear 19. This diagnostic table tilting mechanism per se is the same as in the prior art.

If a chest radiography is to be taken by using the X-ray imaging equipment 1, first the X-ray tube 11, the tabletop 5 of the diagnostic table, and the X-ray flat panel detector 9 are rotated together such that the tabletop 5 of the diagnostic table is stood upright by using the diagnostic table tilting function, and then the tabletop 5 of the diagnostic table is withdrawn. The subject faces a box of the X-ray flat panel detector 9 like the normal chest radiographic plate, then holds the box under his or her both arms, and then puts and fixes his or her chin on a chin holder 17 while facing forward. Then, the X-ray is irradiated by the X-ray tube 11 from the back of the subject and then X-ray images are collected by the X-ray flat panel detector 9.

In this manner, according to the X-ray:imaging equipment according to the first embodiment, since the tabletop of the diagnostic table can be withdrawn in the chest radiography of the subject, the X-ray flat panel detector can be handled in the same way as the normal chest radiographic plate. As a result, unless the subject turns his or her face right or left or stands to face the X-ray source, he or she can be subjected to the radiography in the same posture as the chest radiography in the prior art.

In this case, in addition to the usual hinge shown in FIG. 4, a link type hinge, a round-head hinge, etc. which can support both upper and lower ends rotatably may be employed as the hinge. Moreover, a rail on which a tabletop slides to withdraw may be employed instead of the hinges.

Figure 5:
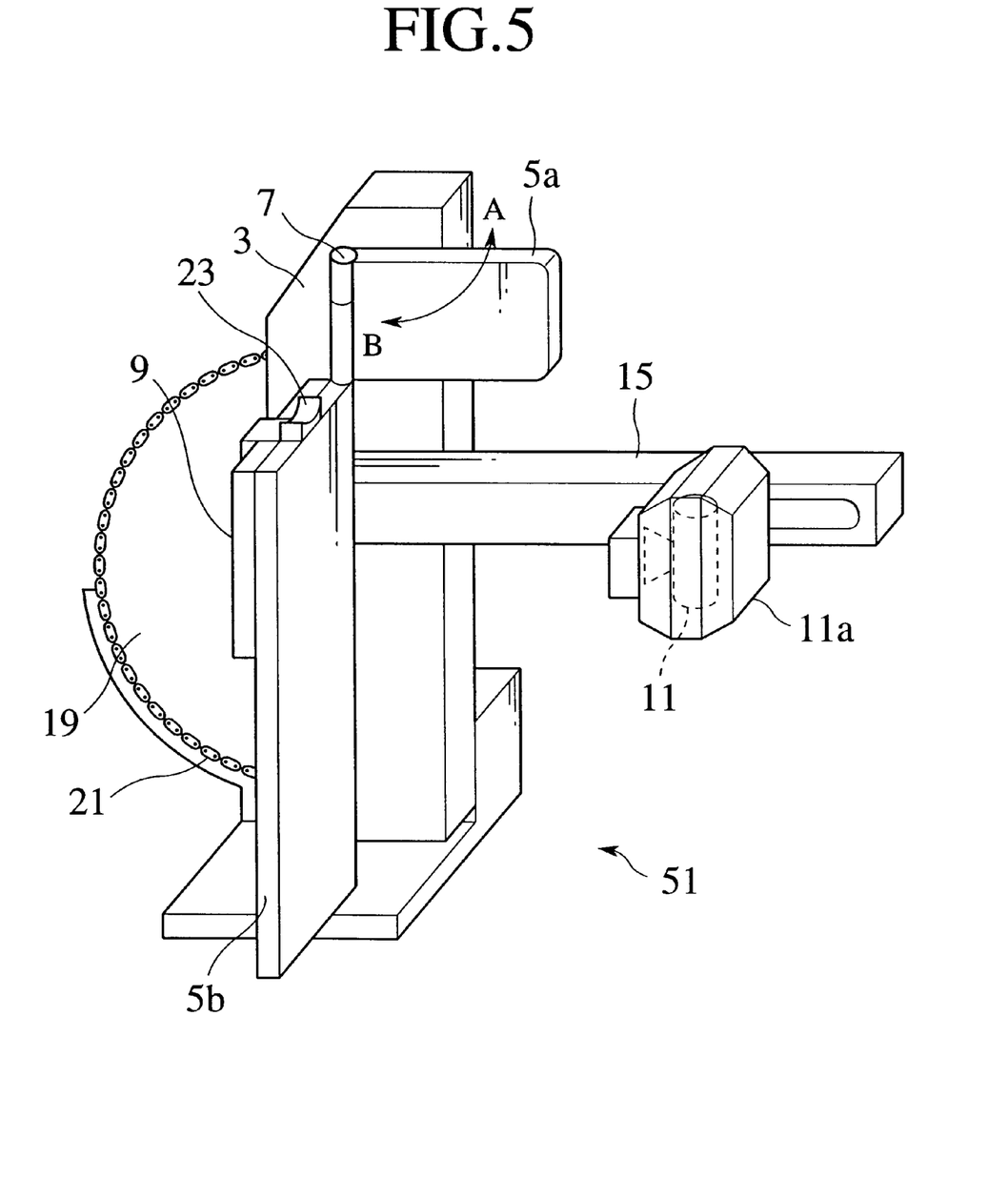
FIG. 5 is a perspective view showing an X-ray imaging equipment according to a second embodiment of the present invention.

FIG. 5 is a perspective view showing an X-ray imaging equipment according to a second embodiment of the present invention, wherein a diagnostic table is positioned upright and also a part of a tabletop of a diagnostic table which is separated into plural parts is withdrawn.

In FIG. 5, an X-ray imaging equipment 51 comprises a main body 3 of a diagnostic table apparatus having a diagnostic table tilting function, a tabletop 5 of a diagnostic table which can be separated into an upper portion 5a and a lower portion 5b, a hinge 7 as a diagnostic table withdrawing means for fitting the upper portion 5a of the tabletop 5 of the diagnostic table rotatably to the main body 3 of the diagnostic table apparatus, an X-ray flat panel detector 9, an X-ray tube 11 covered with a tube cover 11a, and a supporting body 15 for connecting the X-ray flat panel detector 9 and the X-ray tube 11 to the main body 3 of the diagnostic table apparatus.

The second embodiment of the present invention is substantially identical to the first embodiment other than a withdrawing structure for the tabletop of the diagnostic table. Differences between the second embodiment and the first embodiment are two respects described in the following.

The first respect is that the tabletop 5 of the diagnostic table can be separated into the upper portion 5a and the lower portion 5b and only the upper portion 5a of the tabletop 5 can be withdrawn by the hinge 7 as represented by the bi-directed line A-B in FIG. 5.

The second respect is that, when the upper portion 5a of the tabletop 5 of the diagnostic table is withdrawn, a chin holder 23 usually retreated at the back of the X-ray flat panel detector 9 can be pulled out on an upper end of the lower portion 5b of the tabletop 5 of the diagnostic table.

In the case of the chest radiography by using the X-ray imaging equipment, the X-ray tube 11, the tabletop 5 of the diagnostic table, and the X-ray flat panel detector 9 are rotated together such that the surface of the tabletop 5 of the diagnostic table can be perpendicularly positioned by the diagnostic table tilting function, and then the upper portion 5a of the tabletop 5 of the diagnostic table is withdrawn and also the chin holder 23 is pulled out. The subject stands opposite to a box of the X-ray flat panel detector 9 similarly to the normal chest radiographic plate, then holds the box under his or her both arms, and then puts and fixes his or her chin on the chin holder 23 while looking frontward. Then, the X-ray is irradiated by the X-ray tube 11 from the back of the subject and then X-ray images are collected by the X-ray flat panel detector 9.

In this way, according to the X-ray imaging equipment according to the second embodiment, since a part of the tabletop of the diagnostic table can be withdrawn in the chest radiography of the subject, the X-ray flat panel detector can be handled in the same way as the normal chest radiographic plate. As a result, unless the subject turns his or her face right or left or stands to face the X-ray source, he or she can be subjected to the radiography in the same posture as the chest radiography in the prior art.

Figure 6:
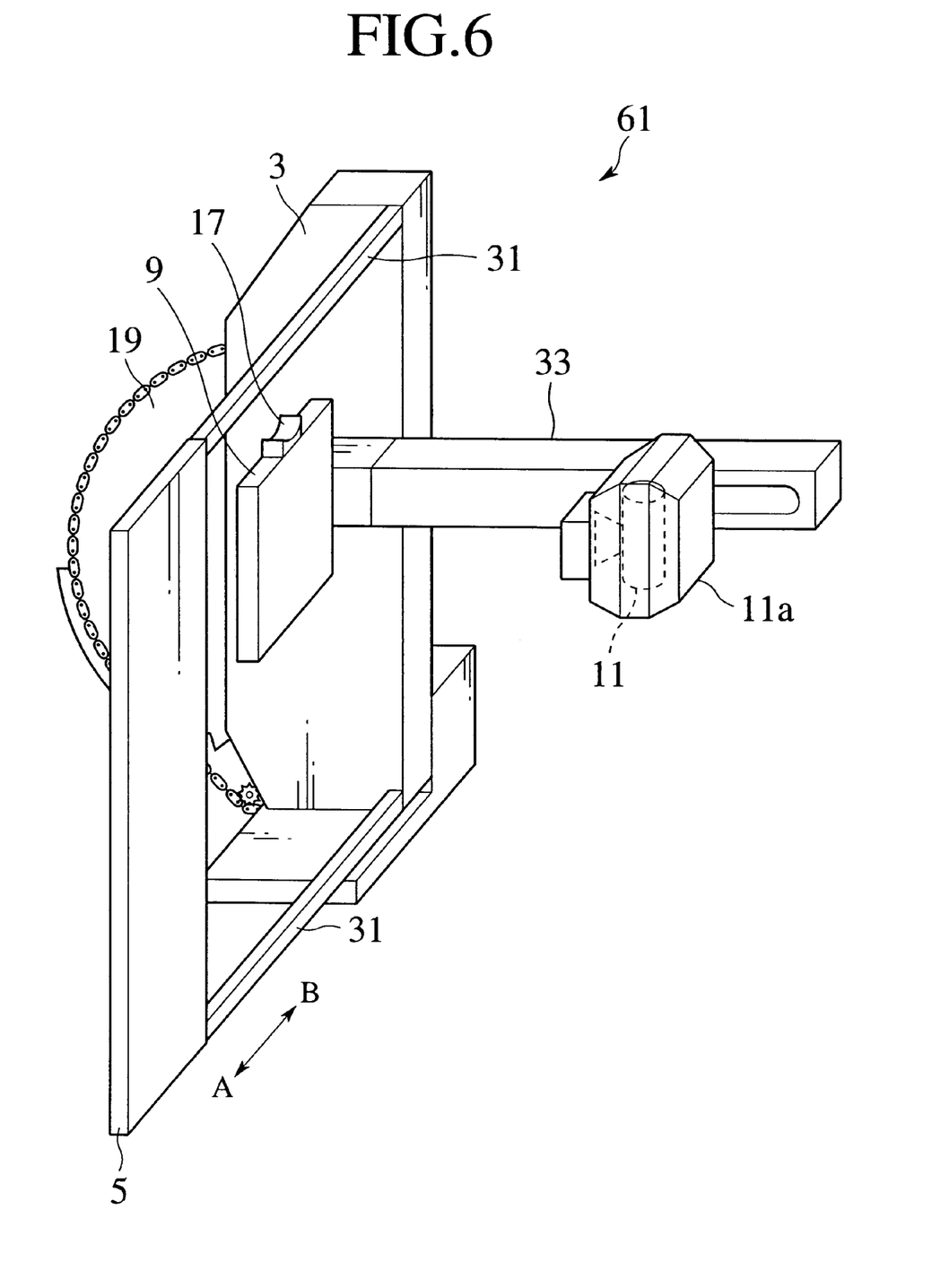
FIG. 6 is a perspective view showing an X-ray imaging equipment according to a third embodiment of the present invention.

FIG. 6 is a perspective view showing an X-ray imaging equipment according to a third embodiment of the present invention, wherein a diagnostic table is positioned upright and also a tabletop of a diagnostic table is withdrawn in parallel with its surface.

In FIG. 6, an X-ray imaging equipment 61 comprises a main body 3 of a diagnostic table apparatus having a diagnostic table tilting function, a tabletop 5 of a diagnostic table, two rails 31 as a diagnostic table withdrawing means for fitting the tabletop 5 of the diagnostic table slidably to the main body 3 of the diagnostic table apparatus, an X-ray flat panel detector 9, an X-ray tube 11 cornered with a tube corner 11a, and a supporting body 33 for connecting the X-ray flat panel detector 9 and the X-ray tube 11 to the main body 3 of the diagnostic table apparatus.

The X-ray imaging equipment 61 is the so-called overtable tube type X-ray imaging equipment wherein, when the tabletop 5 of the diagnostic table is positioned horizontally, the X-ray tube 11 is positioned on a front surface side (upper side) of the tabletop 5 of the diagnostic table. The X-ray tube 11 is fitted to the main body 3 of the diagnostic table apparatus via the supporting body 33 such that it can be moved relative to the tabletop 5 of the diagnostic table in the vertical and longitudinal directions respectively.

The X-ray flat panel detector 9 is formed by installing a detector as shown in FIG. 3, for example, into a box acting also as a shielding. The X-ray flat panel detector 9 is displaced to face the X-ray tube 11 via the tabletop 5 of the diagnostic table such that it can be moved together with a movement of the X-ray tube 11 along the longitudinal direction of the tabletop 5 of the diagnostic table. A chin holder 17 which holds a chin of the subject thereon at the time of the chest radiography is provided on a top of the X-ray flat panel detector 9.

The tabletop 5 of the diagnostic table is fitted to the main body 3 of the diagnostic table apparatus by two rails 31 provided in parallel with a short side of the tabletop 5. In the chest radiography, the tabletop 5 of the diagnostic table can be slid along the rails 31 in the direction indicated by an arrow A, so that it can be withdrawn from an irradiation path from the X-ray tube 11 to the X-ray flat panel detector 9.

In the case of the chest radiography by using this X-ray imaging equipment 61, the X-ray tube 11, the tabletop 5 of the diagnostic table, and the X-ray flat panel detector 9 are rotated together such that the surface of the tabletop 5 of the diagnostic table can be perpendicularly positioned by the diagnostic table tilting function, and then the tabletop 5 of the diagnostic table is withdrawn along the rails 31. The subject stands opposite to a box of the X-ray flat panel detector 9 like the normal chest radiographic plate, then holds the box under his or her both arms, and then puts and fixes his or her chin on the chin holder 17 while looking frontward. Then, the X-ray is irradiated by the X-ray tube 11 from the back of the subject and then X-ray images are collected by the X-ray flat panel detector 9.

In this way, according to the X-ray imaging equipment according to the third embodiment, since the tabletop of the diagnostic table can be slid and withdrawn in the chest radiography of the subject, the X-ray flat panel detector can be handled in the same way as the normal chest radiographic plate. As a result, unless the subject turns his or her face right or left or stands to face the X-ray source, he or she can be subjected to the radiography in the same posture as the chest radiography in the prior art.

As a modified embodiment, the upper portion 5a of the tabletop of the diagnostic table in the second embodiment can also be withdrawn by sliding along the rails, same as in the third embodiment.

Figure 7A:
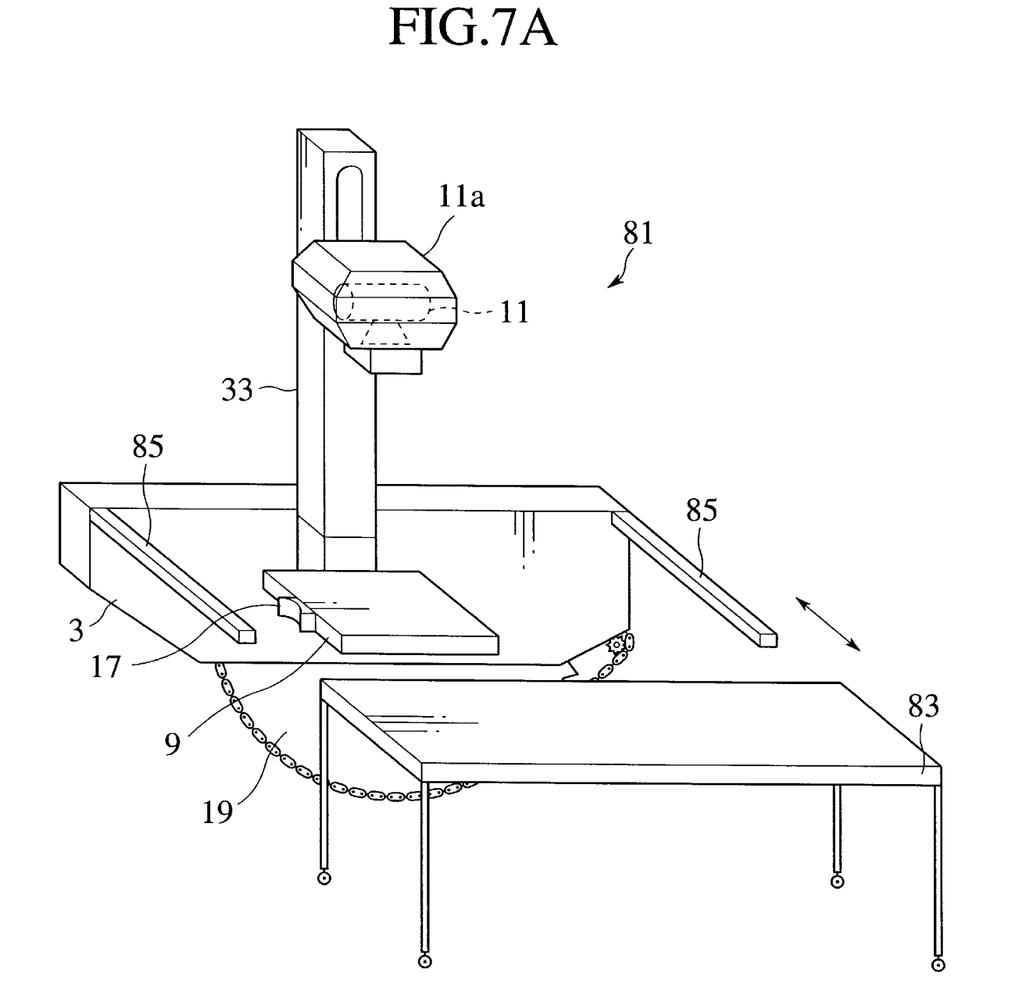
FIGS. 7A and 7B are perspective views showing an X-ray imaging equipment according to a fourth embodiment of the present invention.
Figure 7B:
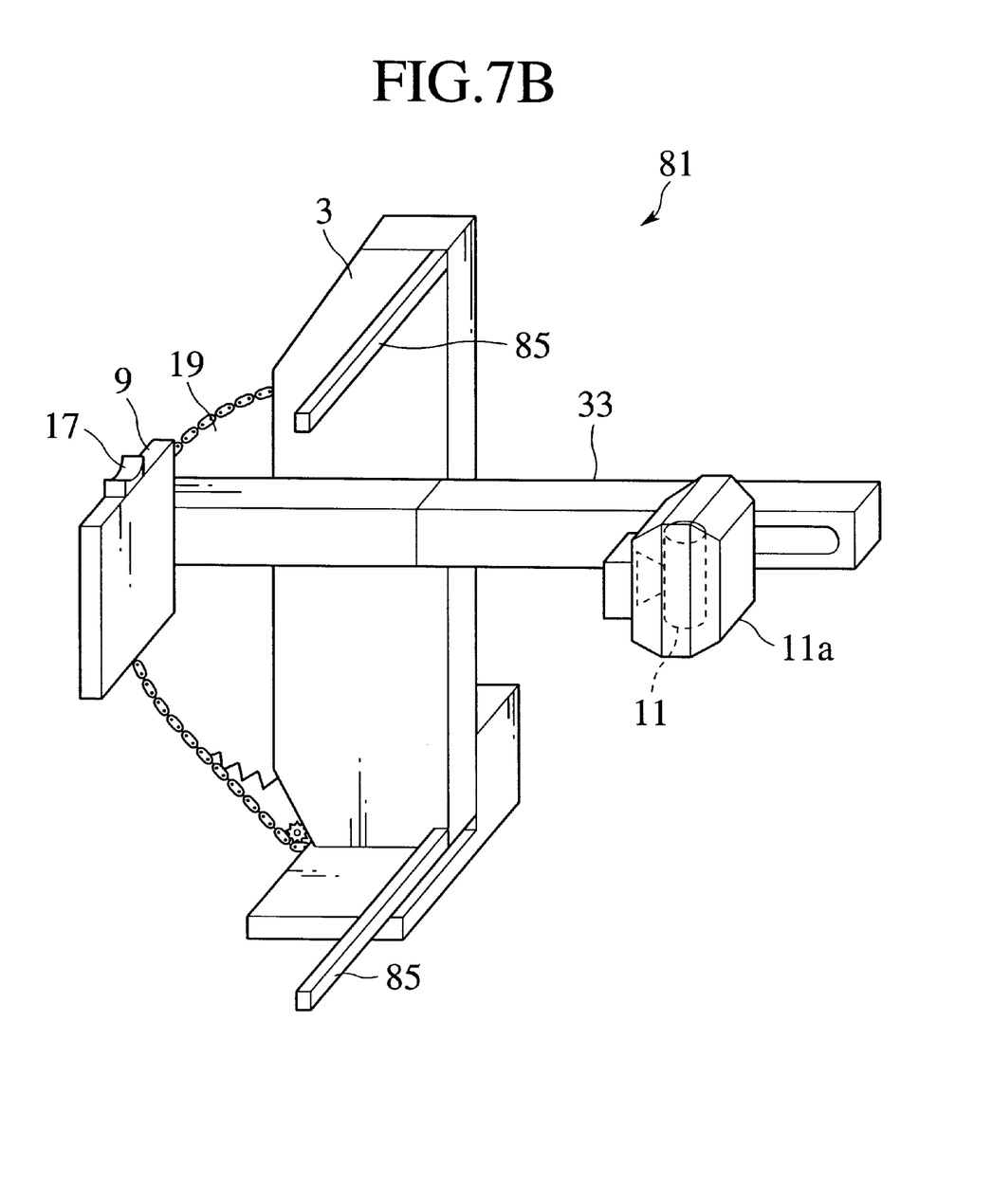

FIGS. 7A and 7B are perspective views showing an X-ray imaging equipment according to a fourth embodiment of the present invention. Especially, FIG. 7A shows the case where the X-ray imaging equipment is employed as a usual radiography/fluoroscopy system, and FIG. 7B shows the case where the X-ray imaging equipment is employed as a chest radiography system.

In FIGS. 7A and 7B, an X-ray imaging equipment 81 comprises a main body 3 of a diagnostic table apparatus having a diagnostic table tilting function, a diagnostic table 83 having legs with casters, two diagnostic table holding arms 85 for fitting the diagnostic table 83 to the main body 3 of the diagnostic table apparatus, an X-ray flat panel detector 9, an X-ray tube 11 cornered with a tube corner 11a, and a supporting body 33 for connecting the X-ray flat panel detector 9 and the X-ray tube 11 to the main body 3 of the diagnostic table apparatus.

The diagnostic table 83 for carrying a subject thereon can move around smoothly in a diagnostic room since it has the legs with the casters. In the radiography/fluoroscopy, first the subject is put on the diagnostic table 83 for carrying a subject thereon at the position separated from the main body 3 of the diagnostic table apparatus, and then the subject together with the diagnostic table 83 for carrying a subject thereon is moved. Then, the diagnostic table 83 on which the subject is laid down is loaded on the diagnostic table holding arms 85 and fixed thereto. In operation of the X-ray imaging equipment, the diagnostic table 83 for carrying a subject thereon can be fixed to the diagnostic table holding arms 85 by a locking mechanism. Then, after the diagnostic table 83 for carrying a subject thereon has been fixed to the diagnostic table holding arms 85, the diagnostic table 83 for carrying a subject thereon can be installed by folding its legs like a stretcher. Otherwise, the diagnostic table 83 for carrying a subject thereon is so constructed that the legs thereof are detachable and thus only the tabletop of the diagnostic table 83 whose legs are removed can be attached to the diagnostic table holding arms 85.

When the diagnostic table 83 for carrying a subject thereon is installed onto the diagnostic table holding arms 85, a rotation angle of the main body 3 of the diagnostic table apparatus is adjusted such that two diagnostic table holding arms 85 are displaced horizontally relative to a floor surface and simultaneously a height of the diagnostic table holding arms 85 is adjusted in response to a height of the diagnostic table 83 for carrying a subject thereon.

Figure 8A:
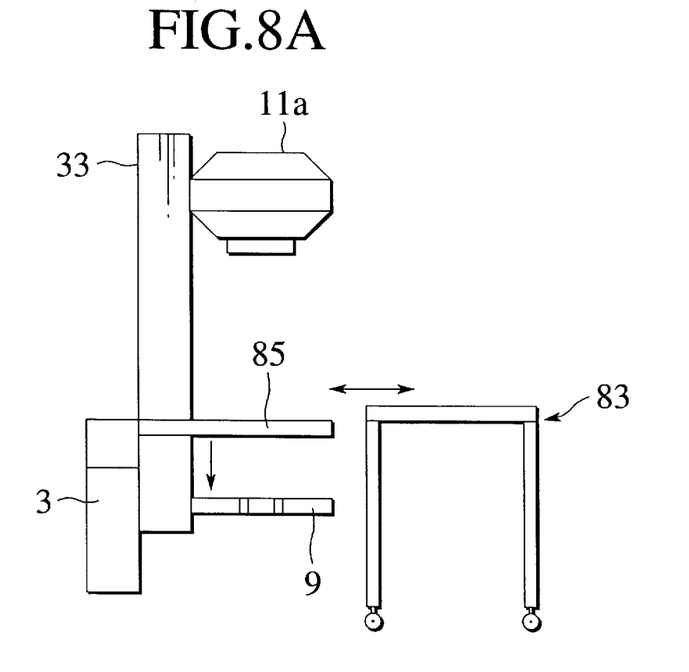
FIGS. 8A and 8B are perspective views showing an attaching/detaching operation of a diagnostic table in the fourth embodiment of the present invention.
Figure 8B:
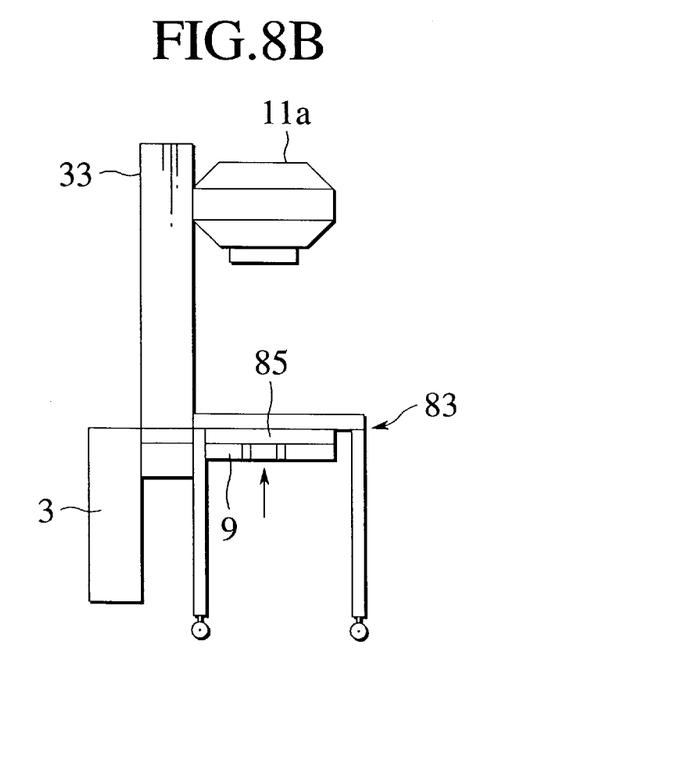

As shown in FIG. 8A, the X-ray flat panel detector 9 is withdrawn downward at the time of an attaching/detaching operation of the diagnostic table 83 for carrying a subject thereon. After the diagnostic table 83 for carrying a subject thereon has been fitted, as shown in FIG. 8B, the X-ray flat panel detector 9 being withdrawn is moved upward to return to a predetermined position. For example, detection of the position can be done by providing a detector.

As shown in FIG. 7B, since the distance between the X-ray flat panel detector 9 and the X-ray tube 11 must be kept sufficiently at the time of the chest radiography, the distance between them (about 2 m) can be maintained by moving not only the X-ray tube 11 but also the X-ray flat panel detector 9. In connection with this, if the main body 3 of the diagnostic table apparatus is tried to be rotated in such chest radiography, there is a possibility that the X-ray flat panel detector 9 or the X-ray tube 11 collides with a floor or a ceiling. Therefore, it is preferable that, if the distance between the X-ray flat panel detector 9 and the X-ray tube 11 is in excess of a predetermined value, a safety device to prevent a rotation of the main body 3 of the diagnostic table apparatus should be provided.

In the chest radiography, the diagnostic table holding arms 85 may be put away.

According to the fourth embodiment, like the above embodiments, an advantage to facilitate the chest radiography can be achieved and following advantages can also be achieved. In other words, since the diagnostic table can be separated, a space around the X-ray imaging equipment can be assured widely. Also, since the subject can be put on the diagnostic table or taken down from the diagnostic table at the position remote from the X-ray imaging equipment, the diagnostic table can be loaded onto the X-ray imaging equipment or unloaded from the X-ray imaging equipment in the situation that the subject is laid down on the diagnostic table.

If a plurality of diagnostic tables are prepared, the subject can be exchanged smoothly. In particular, if the subject is a patient who has troubles in his or her physical behaviors, trouble operations of putting the patient onto the diagnostic table as well as pains of the patient can be reduced.

Figure 9:
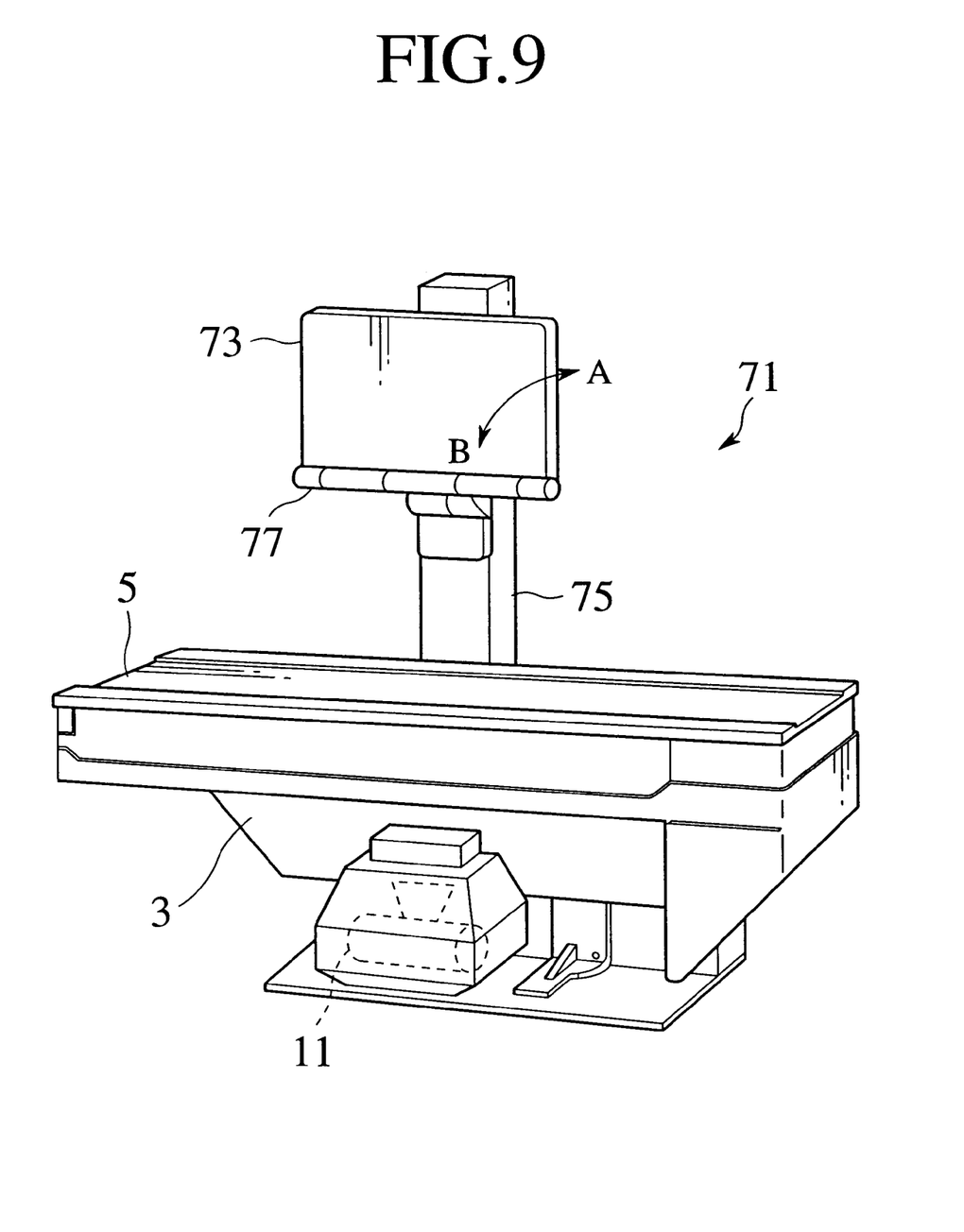
FIG. 9 is a perspective view showing an X-ray imaging equipment according to a fifth embodiment of the present invention.

FIG. 9 is a perspective view showing an X-ray imaging equipment according to a fifth embodiment of the present invention, wherein an X-ray flat panel detector is withdrawn.

In FIG. 9, an X-ray imaging equipment 71 comprises a main body 3 of a diagnostic table apparatus having a diagnostic table tilting function, a tabletop 5 of a diagnostic table, an X-ray flat panel detector 73, an X-ray tube 11 cornered with a tube corner 11a, a supporting body 75 for connecting the X-ray flat panel detector 73 and the X-ray tube 11 to the main body 3 of the diagnostic table apparatus, and a hinge 77 as an X-ray flat panel detector withdrawing means for fitting the X-ray flat panel detector 73 rotatably to the supporting body 75.

The X-ray imaging equipment 71 is the so-called under-table tube type X-ray imaging equipment wherein, when the tabletop 5 of the diagnostic table is positioned horizontally, the X-ray tube 11 is positioned on a back surface side (lower side) of the tabletop 5 of the diagnostic table.

The X-ray tube 11 is fitted to the main body 3 of the diagnostic table apparatus via the supporting body 75 such that it can be moved relative to the tabletop 5 of the diagnostic table in the vertical and longitudinal directions respectively.

The X-ray flat panel detector 73 is formed by installing a detector as shown in FIG. 3, for example, into a box acting also as a shielding. The X-ray flat panel detector 73 is displaced to face the X-ray tube 11 via the tabletop 5 of the diagnostic table such that it can be moved together with a movement of the X-ray tube 11 along the longitudinal direction of the tabletop 5 of the diagnostic table.

The hinge 77 is provided to a side of the X-ray flat panel detector 73 located on the supporting body 75 side. Hence, the X-ray flat panel detector 73 can be rotated in the direction indicated by an arrow A, so that it can be withdrawn from an irradiation path from the X-ray tube 11 to the X-ray flat panel detector 73.

In the case of the X-ray radiography/fluoroscopy by using this X-ray imaging equipment 71 of the fifth embodiment, first the X-ray flat panel detector 73 is rotated in the direction indicated by an arrow A to withdraw, then the subject is laid down on the tabletop 5 of the diagnostic table in the situation that no obstacle is present over the tabletop 5 of the diagnostic table. After such preparation has been finished, the X-ray flat panel detector 73 is rotated in the direction indicated by an arrow B to fall down to a position parallel with the tabletop 5 of the diagnostic table, and then X-ray images can be collected. In case a necessity of accessing of a doctor or a technical expert to the subject is caused in the middle of the X-ray radiography/fluoroscopy, a wide working space can be assured by rotating the X-ray flat panel detector 73 in the direction indicated by an arrow A.

As described above, according to the present invention, because the thin X-ray flat panel detector is employed, the distance between the X-ray tube and the detector can be kept sufficiently in the chest radiography.

Also, according to the present invention, there can be achieved an advantage that, because the diagnostic table can be withdrawn, interference of the diagnostic table with the face of the subject can be eliminated at the time of the chest radiography and the radiography of the subject in his or her relaxed posture can be taken.

According to the present invention, since the diagnostic table can be separated, a space around the X-ray imaging equipment can be assured widely. Also, since the subject can be put on the diagnostic table or taken down from the diagnostic table at the position remote from the X-ray imaging equipment, the diagnostic table can be loaded onto the X-ray imaging equipment or unloaded from the X-ray imaging equipment in the situation that the subject is laid down on the diagnostic table. If a plurality of diagnostic tables are prepared, the subject can be exchanged smoothly. In particular, if the subject is a patient who has troubles in his or her physical behaviors, trouble operations of putting the patient onto the diagnostic table as well as pains of the patient can be reduced.

Further, according to the present invention, since the X-ray flat panel detector can be withdrawn from the upper portion of the diagnostic table, there can be achieved an advantage that it becomes easy for the subject whose physical strength is declined and the handicapped subject to board or get off the diagnostic table and that it becomes easy for a doctor or a technical expert to get access to the subject.

Furthermore, according to the present invention, in the radiography/fluoroscopy after the X-ray flat panel detector has been returned from its withdrawn state, there can be achieved an advantage that, since only the thin and light-weight X-ray flat panel detector must be positioned over the subject, a coercive impression against the subject can be eliminated and safety can be improved.

It should be understood that many modifications and adaptations of the invention will become apparent to those skilled in the art and it is intended to encompass such obvious modifications and changes in the scope of the claims appended hereto.

What is claimed is:

1. An X-ray imaging equipment comprising:
   a tabletop of a diagnostic table on which a subject is loaded;
   an X-ray generating means provided on a front surface end of the tabletop of the diagnostic table;
   an X-ray flat panel detector provided on a back surface end of the tabletop of the diagnostic table;
   a supporting body for holding the X-ray generating means and the X-ray flat panel detector so as to face each other; and
   a tabletop supporting means for supporting the tabletop of the diagnostic table so as to be turned around an axis which is parallel with a long side of the tabletop of the diagnostic table and thus to be withdrawn from an X-ray irradiating path from the X-ray generating means to the X-ray flat panel detector.

2. An X-ray imaging equipment comprising:
   a tabletop of a diagnostic table on which a subject is loaded and which can be split into at least two parts;
   an X-ray generating means provided on a front surface end of the tabletop of the diagnostic table;
   an X-ray flat panel detector provided on a back surface end of the tabletop of the diagnostic table;
   a supporting body for holding the X-ray generating means and the X-ray flat panel detector so as to face each other; and
   a tabletop supporting means for supporting the tabletop of the diagnostic table so as to be able to withdraw a portion of the tabletop of the diagnostic table in a state that the diagnostic table is in a vertical position, the portion corresponding to a head of the subject in a standing position.

3. An X-ray imaging equipment according to claim 2, wherein the tabletop supporting means turns the portion of the tabletop of the diagnostic table, which corresponds to the head of the subject, around an axis which is parallel with a long side of the tabletop of the diagnostic table.

4. An X-ray imaging equipment according to claim 2, wherein the tabletop supporting means moves the portion of the tabletop of the diagnostic table, which corresponds to the head of the subject, in parallel with its tabletop surface.

5. An X-ray imaging equipment comprising:
   a tabletop of a diagnostic table on which a subject is loaded;
   an X-ray generator provided on a front surface end of the tabletop of the diagnostic table;
   an X-ray flat panel detector provided on a back surface end of the tabletop of the diagnostic table;
   a supporting body configured to hold the X-ray generator and the X-ray flat panel detector so as to face each other; and
   a tabletop configured to support the tabletop of the diagnostic table so as to be turned around an axis parallel with a long side of the tabletop of the diagnostic table and thus to be withdrawn from an X-ray irradiating path from the X-ray generator to the X-ray flat panel detector.

6. An X-ray imaging equipment comprising:
   a tabletop of a diagnostic table on which a subject is loaded and which can be split into at least two parts;
   an X-ray generator provided on a front surface end of the tabletop of the diagnostic table;
   an X-ray flat panel detector provided on a back surface end of the tabletop of the diagnostic table;
   a supporting body configured to hold the X-ray generator and the X-ray flat panel detector so as to face each other; and
   a tabletop support configured to support the tabletop of the diagnostic table so as to be able to withdraw a portion of the tabletop of the diagnostic table in a state that the diagnostic table is in a vertical position, the portion corresponding to a head of the subject in a standing position.

7. An X-ray imaging equipment according to claim 6, wherein the tabletop support turns the portion of the tabletop of the diagnostic table, which corresponds to the head of the subject, around an axis which is parallel with a long side of the tabletop of the diagnostic table.

8. An X-ray imaging equipment according to claim 6, wherein the tabletop support moves the portion of the tabletop of the diagnostic table, which corresponds to the head of the subject, in parallel with its tabletop surface.

* * * * *